Figure 1:
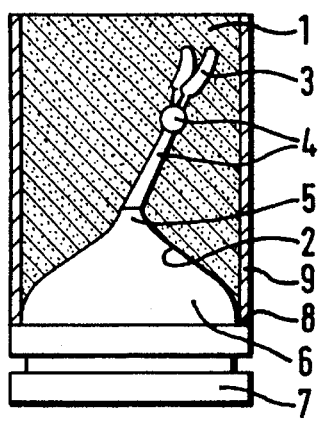

United States Patent [19]
Thomsen

[11] Patent Number: 5,609,483
[45] Date of Patent: Mar. 11, 1997

[54] PROCESS FOR DOCUMENTING THE PRODUCTION OF A DENTAL CAST OBJECT

[76] Inventor: Peter K. Thomsen, Wiesenweg 7 24113, Molfsee/Schulensee, Germany

[21] Appl. No.: 324,767

[22] Filed: Oct. 17, 1994

[30] Foreign Application Priority Data

Oct. 18, 1993 [EP] European Pat. Off. ............ 93116811

[51] Int. Cl.⁶ ................................................. A61C 13/08
[52] U.S. Cl. ..................................... 433/202.1; 433/213
[58] Field of Search ............................ 264/16; 433/213, 433/214, 202.1, 34; 249/53 R, 54, 134, 163

[56] References Cited

U.S. PATENT DOCUMENTS

| | | | |
|---|---|---|---|
| 4,324,546 | 4/1982 | Heitlinger | 433/213 X |
| 4,508,155 | 4/1985 | Rousseau | 164/35 |
| 4,603,728 | 8/1986 | Rousseau | 164/237 |
| 4,611,288 | 9/1986 | Duret et al. | 433/213 X |
| 4,749,020 | 6/1988 | Rousseau | 164/237 |
| 5,092,022 | 3/1992 | Duret | 433/213 X |
| 5,183,095 | 2/1993 | Sullivan | 249/134 X |
| 5,224,049 | 6/1993 | Mushabac | 433/34 X |
| 5,324,186 | 6/1994 | Bakanowski | 249/54 X |

FOREIGN PATENT DOCUMENTS

| | | | |
|---|---|---|---|
| 2516786 | 5/1983 | France | A61C 13/20 |
| WO-A-83/04198 | 12/1983 | WIPO | B22C 7/02 |

*Primary Examiner*—Robert P. Swiatek
*Assistant Examiner*—Yvonne R. Abbott
*Attorney, Agent, or Firm*—Chilton, Alix & Van Kirk

[57] ABSTRACT

A process for documenting the position of a dental casting model relative to the mold surface is distinguished by the fact that the position of the model on the gate molder is pictorially recorded prior to it being embedded. This is expediently done simultaneously to the pictorial fixing of a marking which reproduces the position of the surface of an assigned mold in relation to the cast object or to the gate molder. This can be a marking which is physically connected to the gate molder. However, it can also be contained in the recording instrument or stored in the analyzing unit of the recording instrument. Where different sizes are used, the assignment of the respectively pertinent marking to the gate molder of predetermined size can be realized automatically. Instead of the use of such a marking, it is also possible additionally to take a pictorial record of the mold following the embedding, in order to be able to interrelate the position of the object and the position of the mold surfaces by comparing the records prior to and following the embedding. Instead of this, it is also possible to document the model in the actually used muffle mold shell or to document the model or the mold cavity of the finished muffle.

15 Claims, 1 Drawing Sheet

U.S. Patent    Mar. 11, 1997    5,609,483

PROCESS FOR DOCUMENTING THE PRODUCTION OF A DENTAL CAST OBJECT

For faults on dental prostheses, which are created in the metal-casting procedure, it is generally the dental technician—not always justly—who is held responsible. His own interest—as well, however, as a prominently defined statutory duty—demand of him the widest possible documentation of the production run, including adherence to the material-working guidelines prescribed to him by the manufacturer of the casting alloy used. A particularly important role in this is played by the proper arrangement of the casting models in the dead casting mold, since a defective arrangement can result in porosity and shrinkage cavitation (information document "The exact-fitting dental cast" issued by Heraeus Edelmetalle GmbH, Hanau).

For the production of the casting mold, a wax model of the article to be cast and of the associated runners is initially produced and fastened head-down on a model of the pouring gate, which model serves as a base. This pouring gate is hereinafter referred to simply as a gate molder. The model which is thus produced is then embedded in a molding compound, which is allowed to harden, then, following the removal of the gate molder, is heated up, during which process the model compound burns, and is finally, by centrifugal casting or vacuum die-casting methods, filled with the molten metal. Of importance to the quality of the cast object is its position in relation to the outer face of the mold, in the direction of which the melting heat is evacuated (WO-8304198). If the cast object, in relation to other parts of the cast or to other cast objects in the same mold, is not situated close enough to the mold surface, then it may happen that it rigidifies, in part, only after other castings, and shrinkage cavities are formed in this process. The mold generally has no optional external shape; rather, the external shape of the mold is prescribed, when the model is embedded into the compound forming the mold, by so-called "casting rings" or "muffle-molders" or simply "paper sleeves", which are placed onto the gate molders, serving as bases, and are hereinafter referred to, in aggregate, as "muffle mold shell". Just a few types and sizes of muffle mold shells are in use, possessing essentially the same height and stepped diameters. For instance, from a leading manufacturer there are muffle mold shells having four different inside diameters and the same height, from another manufacturer three sizes. To each size there is assigned a suitably fitting gate molder, onto which the associated muffle mold shell can be placed in a fitting manner. In preparing the model, the dental technician therefore chooses the gate molder, which is used as a base, according to the necessary size of the muffle mold shell and, in constructing the wax model onto the gate molder, envisages the external shape of the mold which will subsequently be produced, so as to predetermine the correct distance of his cast object from the outer face. Useful to him in this can be a muffle mold half-shell, which is used purely in the construction of the model and which he can place onto the gate molder used as a base so as to be able to check by it the height of the model (with regard to the subsequent distance of the object from the bottom face of the mold) and the peripheral distance.

The invention proposes to document this state of the casting model, prior to being embedded, pictorially in such a way that the position of the model in relation to the surface of the mold can be directly or indirectly deduced therefrom. This can be done by a marking being depicted with the model, which marking reproduces the position of the mold. Where the gate molder permits conclusions to be drawn about the size and position of the muffle mold shell, the documentation of the gate molder, with the model, is also sufficient, since the relative position of the model to the gate molder permits conclusions to be drawn about the position of the model in the subsequent casting mold. For example, the model and the gate molder can be depicted on one and the same photographic record. Where a gate molder is used which can be combined with muffle mold shells of different size or in which the muffle mold shell can be filled to a varied extent with molding compound, the mold, following the embedding (expediently prior to removal of the casting gate molder), can also be pictorially recorded. The comparison of the depictions of the model prior to the embedding and of the mold following the embedding then allows a conclusion to be drawn about the mutual relative position. Where a casting gate molder is used which can be combined with muffle mold shells of different size, according to the invention there can be attached to the gate molder a device for determining the size of the envisaged muffle mold shell and this can be pictorially recorded with the model. The chosen method for the pictorial documentation is of little importance in this context. Using known instruments, photographs can be easily produced and subsequently easily analyzed, which photographs expediently show the object from different aspects (for example, from the direction of the three principal axes). Photographic representations can also be stored in a paperless manner by electronic data-processing means. In order to reduce the necessary storage space, it can also be expedient to choose a scanning and representation mode in which only the outlines of the model and, where appropriate, of the gate molder are recorded.

Pertinent scanning and representation means are known. In any event, the gate molder can be included in the depiction in order to establish the vertical position of the model in relation to the gate molder or to the muffle mold shell and to the mold. Where, however, according to a feature of the invention, the recording instrument contains devices for clearly positioning the gate molder in relation to the recording optics, then it is sufficient, where appropriate, to represent only the object and at the same time, in suitable form, provide a marking or numeric reference indicating, directly or indirectly, the position of the gate molder.

Since, with regard to the end purpose of the representation, it is less a matter of the relative position of the model to the gate molder and more a matter of the relative position to the anticipated outer boundary of the mold, a marking is preferred which directly or indirectly allows a conclusion to be drawn about the position of the mold surface. Such a marking is provided, for example, by the abovementioned muffle mold half-shell, which, attached in correct and proper position to the gate molder, can be depicted as a marking with the model. It indicates the position of the outer periphery of the mold. The height to which the mold can be filled can be indicated, such that it is visible from the marking, on the representation.

Where, as already mentioned above as an option, the recording instrument is provided with a device which gives the gate molder a predetermined position in relation to the recording optics, the marking does not need to be provided physically on the model; rather, it can also be part of the recording device or the reproduction material. For example, on the paper recording the impression of the acquired representation, the mold limits for those sizes of muffle mold shells which enter into consideration can be pre-printed, the type and size of the gate molder appearing in the record permitting a conclusion to be drawn as to which of the respectively pre-printed limits is determinant of the respective representation. The marking can also, however, be produced directly in the recording instrument by electronic or other means and stored with the acquired representation. Since the position of this marking to be produced is dependent upon the muffle mold shell to be used, this can, in the recording operation, be manually inputted or, better still, determined directly by the recording apparatus through scanning of the gate molder.

Where it is envisaged that both the model prior to the embedding and the mold following the embedding are documented, the two depictions are expediently stored one above the other, thereby enabling the position of the model to be directly compared with the mold boundaries.

Where records are intended to be taken from different aspects, the recording apparatus can be equipped with mirrors, which are arranged such that the various aspects can be recorded simultaneously for the one fixed recording lens in one representation. Instead, a plurality of lenses or a mobility of the lens into different viewing positions can also be envisaged.

According to a further embodiment of the invention, the model can be depicted for documentation purposes in the muffle mold shell. To this aim, a material can be chosen for the muffle mold shell which is permeable to the image-producing radiation type. Where visible radiation is used, it is created, for example, from glass or transparent plastic. Where it is not transparent, a radiation type which penetrates through it (for example, alpha, beta or gamma radiation) is used. In this way, not only can a top-view representation be acquired, which in any case is not obstructed by the muffle mold shell, but also a side view. Instead, it is also in many cases sufficient, apart from a top view, to produce a view diagonally from above through the fill opening of the muffle mold shell—where appropriate, from different directions—and, where necessary, to reconstruct from this the position of the model in relation to the muffle mold shell.

Finally, it is also possible within the framework of the invention to establish the position of the model or mold cavity or cast object in the finished muffle or mold by suitable radiation (including sound waves.). The use of light rays for video monitoring in dental casting technology is known per se (FR-A-2516786). The same applies to the use of X-rays for the detection of casting faults ("Lab-X708" prospectus issued by J. Morita Europe GmbH, Frankfurt/M).

The documentation of the position of the model, mold cavity or cast object in the muffle mold shell which is actually to be used or in the finished mold avoids the uncertainty regarding the actually used mold size, where, in connection with the gate molder used, differently sized muffle mold shells can be used.

Figure 2:
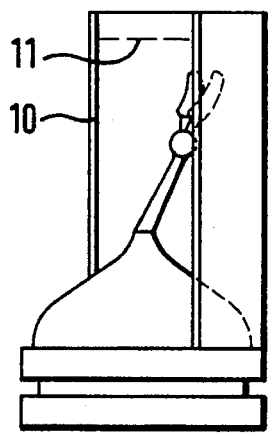
Figure 3:
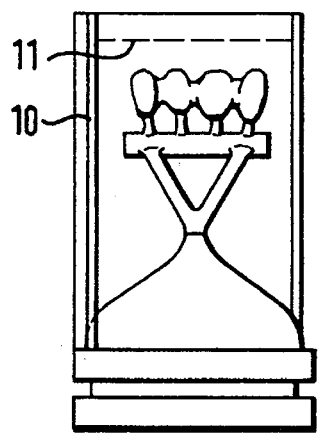
Figure 5:
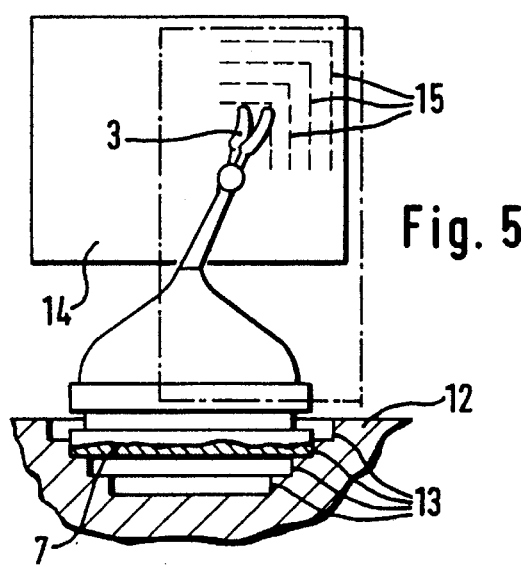
Figure 4:
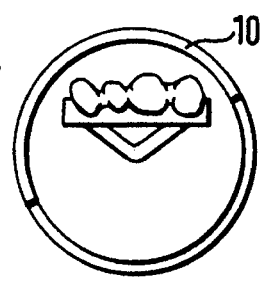
Figure 7:
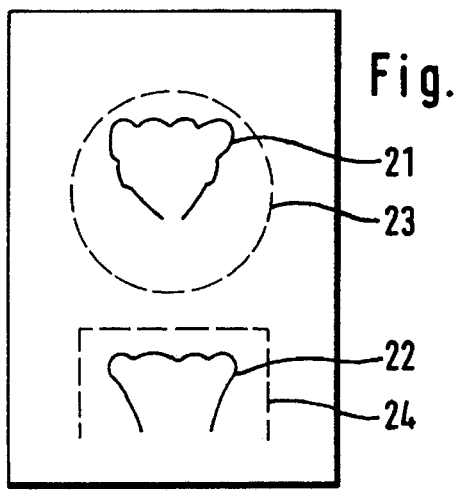
Figure 6:
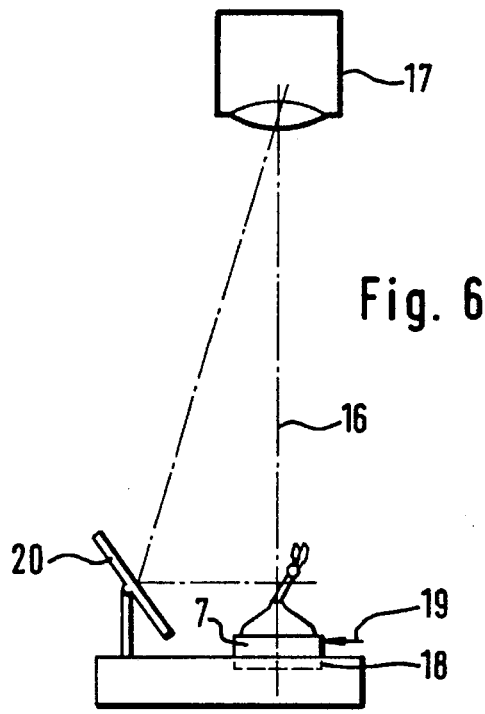

The invention is described in greater detail below with reference to the illustrative embodiment illustrated diagrammatically in the drawing, in which:

FIG. 1 shows a side view of a model, embedded in a mold represented in cut section, FIGS. 2, 3 and 4 show two side views and a top view of a not yet embedded model, FIG. 5 shows the side view of a model in front of a marked screen in the positioning device of a recording apparatus, FIG. 6 shows the diagrammatic representation of a mirrored recording apparatus, and FIG. 7 shows the example of a stored representation.

If the dotted part of the representation in FIG. 1 is taken and rotated through 180°, then the representation is obtained of a mold 1 having a top-sided pouring gate 2, into which the molten metal is poured for the filling of the mold cavity.

For the production of this mold, the wax model 3, with the models 4 of the associated runners, is constructed on the tip 5 of the gate molder 6, which forms the pouring gate 2 and merges downwards into a base 7, which can be differently and suitably shaped so as to interact, for example, with holding, gripping and positioning tools. The gate molder 6 and the base 7 are molded in one piece, for example from plastics material, which can remain as a dead model in the mold and, when the mold is baked, is burnt, or can repeatedly be used and therefore, prior to the mold being used, is removed therefrom. At the transition of the gate molder 6 with the base 7 there is a step 8 forming a seat for a pipe piece 9, which pipe piece forms a mold shell for the molding compound 1 and is therefore referred to here as a muffle mold shell. The gate molder 6, the base 7 and the muffle mold shell 9 have generally the shape of rotation bodies; however, this is not absolutely necessary.

In constructing the wax model 3, 4 on the gate molder 6, the dental technician makes use of the gauging shell 10, which is half a muffle mold shell and, like this, can be placed snugly onto the step 8. It indicates to the technician where in the finished mold its surface is situated and bears a marking 11, indicating the height which the mold 1 shall have. Since the technician knows that the cast object corresponding to the model 3 is supposed, in the mold, to have a specific position relative to the surface of the mold in relation to the other model parts 4, he is able to align the casting model suitably in relation to the half shell.

If the finished model is photographed, prior to the embedding, together with the gauging shell 10, then a precise documentation of the position of the model in the mold 1 is obtained, on the precondition that the position of the model no longer changes during the embedding and that a muffle mold shell corresponding to the gauging shell is used. FIGS. 2, 3 and 4 can be regarded as records of this kind taken from various directions. In order to identify the position of the model in the mold, two of these representations, for example FIG. 4 in conjunction with FIG. 2 or FIG. 3, are sufficient, since it is possible to establish both the distance of the model parts 3 from the circle periphery (FIG. 4) and from the prospective bottom side of the mold (line 11). This is therefore an effective and, at the same time, very simple form of documentation according to the invention. Where the gate molder allows the use of different muffle mold shells, the muffle mold shell which is used in each case can be additionally documented (for example by personally inputted memo).

Whereas, in the aforesaid examples, the gauging shell 10 forms a marking which is connected to the object and allows the position of the object to be determined, this marking can also be part of the recording apparatus. An example is shown by FIG. 5. The recording apparatus exhibits a mounting 12 for the base 7, which mounting is shaped such that bases 7 of four different diameters can be held centred on the steps 13 in recesses of correspondingly different diameters and different heights. Opposite the optics (not illustrated in the drawing) of the recording instrument, there is disposed a screen 14, which possesses markings 15 for the different mold diameters assigned to the steps 13. On a photographic record, which at least approximately captures the face indicated by a dash-dot frame, enough of the base or gate molder is recognized for the diameter to be identified and linked to the associated marking 15. Additionally appearing on the record is the casting model 3, the position of which relative to the associated marking can be determined, from which the corresponding conclusions about the position in the mold can be drawn. The record reveals enough of the model to enable a top view according to FIG. 4, where appropriate, to be dispensed with.

Where there is no wish to dispense with such a top view, then the diagram of the recording instrument according to FIG. 6 is a suitable option. The optical axis 16 of the optics 17 conforms to the longitudinal axis of the recording device 18 for the base 7. The recording device 18 is of centering design and allows the diameter of the base 7 or of other identifying characteristics of the base 7 to be established by means of a scanning device 19 diagrammatically indicated by an arrow. In the simplest case, this scanning device is configured such as has been illustrated in FIG. 5 by the steps 13. Located laterally next to the object to be depicted is a mirror 20, which, just like the object itself, lies within the image-producing range of the optics 17 and is aligned such that, in addition to the directly acquired top view, the depiction also embraces, en route via the mirror 20, a side view. As in the example represented in FIG. 5, a (non-represented) screen can be provided for the creation of the comparison marking for establishing the position of the model. Instead, the analyzing device, which is connected downstream of the optics 17, can also be equipped such that, in the depiction, a marking is automatically produced, which is stored in the analyzing unit for each base size. The scanning device 19 indicates to the analyzing unit the marking which is to be used in each case.

The representation can be a complete photograph. In order to abbreviate the process and reduce the storage requirement, it can also, however, be confined to the outline reproduction as indicated in FIG. 7, where the lines 21 and 22 indicate the top-view and side-view outline respectively of the model and the dashed lines 23 and 24 indicate, as a marking, the associated mold outline.

In the above examples, it has been presupposed that the diameter of the base 7 of the gate molder is in itself sufficient to determine the type and size of the gate molder and of the muffle mold shell to be used therewith. Where different makes of gate molders are used, it may further be necessary to identify also different types of gate molders and associated muffle mold shells. To this end, mold characteristics other than the diameter can, of course, be consulted, for example projections or recesses on the gate molder and on the muffle mold shell which respectively fit only one size of muffle mold shell, the [lacuna] provided on the gate molder becoming visible in the pictorial representation or being scanned and then recorded together with the representation. Finally, it is also conceivable that, in connection with a gate molder of specific diameter, muffle mold shells of different heights can be used; the gate molder can also in this context be provided with identification features which are automatically identifiable in the instrument or are identifiable in the representation and which conform to corresponding features of the muffle mold shell. These can be scanned automatically in the recording instrument or identified by eye in the representation.

Where—as has been indicated above in the preface to the description—apart from the model prior to the embedding, the mold 1 following the embedding is also documented, then this can be done by pictorial recording with or without a gate molder 6 or base 7. The record containing the gate molder or base may be expedient so as to enable a simple measurement comparison to be made. Generally, however, the mold itself also provides adequate measurement pointers, thereby enabling the gate molder and/or the base to be dispensed with.

In those processes according to the invention in which the finished muffle or mold is transilluminated, a side view of the type shown in FIG. 1 and a top view of the type shown in FIG. 4 are obtained. In this context, it is not important whether the muffle mold shell, in this state, is already removed or not.

Where the model is documented prior to being embedded in the muffle mold shell to be used, representations according to FIG. 1 and FIG. 4 are likewise obtained.

I claim:

1. In a process for documenting the production of a dental cast object comprising the steps of creating a model of the object on a gate molder, attaching a muffle mold shell to the gate molder and embedding the model in a molding compound to form a mold, the gate molder determining the position of the muffle mold shell, the improvement comprising pictorially recording the position of the model on the gate molder prior to the embedding of the model by a) providing a marking which indicates the subsequent position, to be adopted, by a substantial part of the surface of the mold, and b) determining the gate molder to be used where the casting gate molder can only be combined with a muffle mold shell of a specific size.

2. The process as claimed in claim 1, wherein the pictorial representation, together with documentation of other production segments, of material specification and/or identification data, is stored by means of a data-processing unit.

3. The process as claimed in claim 1 including the step of pictorially recording the mold following the embedding.

4. The process as claimed in claim 1 including the steps of providing on the gate molder a device for determining the size of the muffle mold shell and pictorially recording the device with the model.

5. In a process for documenting the production of a dental cast object comprising the steps of creating a model of the object on a gate molder, attaching a muffle mold shell to the gate molder and embedding the model in a molding compound, the improvement comprising pictorially recording the position of the model within the muffle mold shell prior to the embedding.

6. The process as claimed in claim 5, wherein the muffle mold shell is made from a material which can be penetrated by image-producing radiation.

7. The process as claimed in claim 5, wherein the pictorial recording of the model is from different directions through an upper opening of the muffle mold shell.

8. In a process for documenting the production of a dental cast object comprising the steps of creating a mold by means of a dead model, the improvement of documenting the position of the dead model within the mold by means of radiation penetrating the mold.

9. An apparatus for documenting the production of a dental cast object from a model comprising a gate molder for holding the model, an image-recording instrument, a holding device (18) for holding the gate molder and model in a predetermined setting relative to the image-recording instrument (17), and scannable identification means on the gate molder, the image-recording instrument being equipped with a scanning device (19) and means for storing the result of the scanning.

10. The apparatus as claimed in claim 9, wherein the image-recording instrument is equipped with adjusting means for automatically adjusting the identification means in dependence upon the type or size of the gate molder.

11. An apparatus for documenting the production of a dental cast object from a model comprising a gate molder for holding the model, an image-recording instrument, a holding device (18) for holding the gate molder and model in a predetermined setting relative to the image-recording instrument (17), and marking means for producing a marking, indicating the position of the surface of a part of a mold for the dental cast object, said marking means being positioned relative to the image-recording instrument and the model to record the marking on a pictorial representation of the model made by the image-recording instrument.

12. An apparatus for documenting the production of a dental cast object from a model comprising a gate molder for holding the model, an image-recording instrument, a holding device (18) for holding the gate molder and model in a predetermined setting relative to the image-recording instrument (17), the image recording instrument comprising means for simultaneously recording the model from different directions.

13. The apparatus as claimed in claim 12, wherein the simultaneous recording means includes at least one mirror (20) for simultaneous recording from different directions.

14. The apparatus as claimed in claim 12, wherein the image-recording instrument is capable of recording a plurality of objects from different directions.

15. The apparatus as claimed in claim 12, wherein the image-recording instrument includes a lens that can be adjusted to different aspects.

\* \* \* \* \*